US011122993B2

United States Patent
Hilton

(10) Patent No.: US 11,122,993 B2
(45) Date of Patent: Sep. 21, 2021

(54) PORTABLE PHOTOGRAMMETRY STUDIO

(71) Applicant: BESPOKE MEDICAL INNOVATIONS PTY LTD, Sydney (AU)

(72) Inventor: John Hilton, Sydney (AU)

(73) Assignee: BESPOKE MEDICAL INNOVATIONS PTY LTD, Sydney (AU)

( * ) Notice: Subject to any disclaimer, the term of this patent is extended or adjusted under 35 U.S.C. 154(b) by 0 days.

(21) Appl. No.: 15/576,052

(22) PCT Filed: May 25, 2016

(86) PCT No.: PCT/AU2016/050400
§ 371 (c)(1),
(2) Date: Nov. 21, 2017

(87) PCT Pub. No.: WO2016/187661
PCT Pub. Date: Dec. 1, 2016

(65) Prior Publication Data
US 2018/0153443 A1 Jun. 7, 2018

(30) Foreign Application Priority Data

May 25, 2015 (AU) .................. 2015901906

(51) Int. Cl.
*A61B 5/107* (2006.01)
*G01B 11/24* (2006.01)
(Continued)

(52) U.S. Cl.
CPC .......... *A61B 5/1079* (2013.01); *A61B 5/1077* (2013.01); *G01B 11/24* (2013.01);
(Continued)

(58) Field of Classification Search
CPC ........ G01B 21/00; G01B 11/00; G01B 11/24; A61B 5/1079
See application file for complete search history.

(56) References Cited

U.S. PATENT DOCUMENTS 6,034,716 A 3/2000 Whiting et al.
8,044,996 B2 * 10/2011 Rice ..................... A61B 5/0059
348/50

(Continued)

FOREIGN PATENT DOCUMENTS

DE 10 2004 052 199 A1 4/2006

OTHER PUBLICATIONS

Supplementary European Search Report, App. No. EP 16 79 8951 dated Oct. 8, 2018.
(Continued)

*Primary Examiner* — Kyle M Lotfi
(74) *Attorney, Agent, or Firm* — Muncy, Geissler, Olds & Lowe, P.C.

(57) ABSTRACT

A portable photogrammetry studio for topographical digitisation of stationary surfaces, such as human body surfaces, including at least one high-resolution digital camera to photograph said surface; one or more light sources capable of illumination of said surface; and a mechanised viewing system that is capable of providing different views of said surface to said camera; such that multiple pictures may be taken of said surface from multiple different positions by each said camera. The human body surface is prepared, preferably by coating with a texturiser.

19 Claims, 6 Drawing Sheets

(51) Int. Cl.
  *G02B 7/182*  (2021.01)
  *H04N 5/225*  (2006.01)
  *H04N 7/18*   (2006.01)
(52) U.S. Cl.
  CPC ......... *G02B 7/1821* (2013.01); *H04N 5/2256* (2013.01); *H04N 7/185* (2013.01)

(56) References Cited

U.S. PATENT DOCUMENTS

| | | | | |
|---|---|---|---|---|
| 8,269,982 | B1* | 9/2012 | Olczak | G01B 11/162 |
| | | | | 356/513 |
| 8,902,195 | B2* | 12/2014 | McGibney | G06F 3/0386 |
| | | | | 250/224 |
| 2003/0169917 | A1* | 9/2003 | Ishiyama | G06K 9/00201 |
| | | | | 382/154 |
| 2004/0041998 | A1 | 3/2004 | Haddad | |
| 2007/0212038 | A1* | 9/2007 | Asai | A61B 5/103 |
| | | | | 396/14 |
| 2009/0076772 | A1* | 3/2009 | Hinshaw | A43B 7/1465 |
| | | | | 702/167 |
| 2010/0238271 | A1 | 9/2010 | Pfeiffer et al. | |
| 2010/0238665 | A1* | 9/2010 | Teather | B32B 15/08 |
| | | | | 362/296.01 |
| 2010/0289886 | A1 | 11/2010 | Fenrich et al. | |
| 2010/0296726 | A1 | 11/2010 | Rutschmann et al. | |
| 2011/0134225 | A1* | 6/2011 | Saint-Pierre | G01B 11/03 |
| | | | | 348/47 |
| 2015/0037022 | A1 | 2/2015 | Low et al. | |

OTHER PUBLICATIONS

Resko et al., "Rotating Periscope Based 3D Sensor," IEEE 2008 Conf. on Human System Interactions, Piscataway, NJ, pp. 779-784 (May 25, 2008).

* cited by examiner

PORTABLE PHOTOGRAMMETRY STUDIO

CROSS REFERENCE TO RELATED APPLICATIONS

This nonprovisional application is a National Stage of International Application No. PCT/AU2016/050400, which was filed on May 25, 2016, and which claims priority to Australian Patent Application No. 2015901906, which was filed in Australia on May 25, 2015, and which are both herein incorporated by reference.

TECHNICAL FIELD

The invention relates to the field of photogrammetry. In particular, the invention relates to a device and process for relatively low cost digitization of human body features for use in designing customised products for e.g. medical devices.

BACKGROUND OF THE INVENTION

There are many types of products where a custom-fitted design is functionally and/or aesthetically superior to generic designs, notably in the medical field. For example, podiatrists provide custom-made orthotics and dentists provide custom-made dental implants and sleeping appliances to aid breathing or teeth alignment. The ability to create a product that matches a given person's physical shape is required or desirable for many products. Custom designs typically deliver better performance. In the field of breathing masks, as used in hospitals or for sleep apnoea sufferers, a custom design can avoid air leakage issues or skin pressure-point issues that are common with generic masks.

3D printers are becoming more common as lower costs are associated with the production of 3D printed items. To create a custom 3D printed item intended to be mated with a part of the body the shape of this body part needs to be digitized to guide the creation of the mating shape of the 3D printed part. A number of 3D scanners suitable for this purpose are commercially available, however these scanners can be difficult to use effectively, often requiring a powerful computer to operate and are expensive.

Many 3D scanners project a moving beam of light or an array of light beams on to the surface that is to be scanned. A camera photographs the resulting scene and software can identify each point on the photograph, and hence the 3D location of that point relative to the camera. For each point, the direction can be triangulated with the direction of the light beam to determine the location of the point on the subject's surface. Scans taken in this way produce a point cloud and software is typically used to combine point clouds from multiple scans to build up a complete and more accurate point cloud.

Photogrammetry similarly uses cameras to take photographs of subjects but instead of one or more beams of light photogrammetry relies on the colour or shade of the subject surface. Software can identify corresponding points on the surface and, given the cameras' positions, the surface points can be triangulated. Moreover, given a significant number of matching points, typically in the hundreds to thousands of points, software can analyse the matching points to determine the relative camera positions. A number of commercial photogrammetry products are available including online services where a set of photographs are uploaded to a server which processes the photographs and provides the resulting point cloud. Point clouds can be further analysed by software to create a corresponding surface.

However, as with 3D scanners it is generally difficult to obtain point clouds with the accuracy and resolution required for a custom product to match a body part.

High end photogrammetry studios, as used by the film industry, are typically located in rooms with a multitude of light sources and multiple high resolution cameras. The subject item is typically a model with suitable surface markings. Considerable care is taken to light and photograph the model to obtain photographs that will provide the best resolution results.

Typically, a multitude of simultaneous photographs ensures consistent lighting. Some photogrammetry systems use mirrors to present two or more views in a single camera shot. However, the resolution of such systems is less than the resolution of a system where a single view of the surface fills the view.

However, the type of facilities described above are not portable and relatively expensive to set up and maintain.

Accordingly, it is an object of the invention to provide a way of capturing scanned surfaces from human bodies that is both portable and less expensive than those associated with the prior art.

SUMMARY OF THE INVENTION

According to a first aspect of the invention, there is provided a portable photogrammetry studio for topographical digitisation of stationary surfaces, such as human body surfaces, that includes: at least one high-resolution digital camera to photograph said surface; one or more light sources capable of illumination of said surface; and a mechanised viewing system that is capable of providing different views of said surface to said camera; such that multiple pictures may be taken of said surface from multiple different positions by each said camera.

Preferably the invention provides a portable photogrammetry studio for topographical digitisation of stationary surfaces, such as human body surfaces, that includes: at least one high-resolution digital camera to photograph said surface; one or more light sources capable of illumination of said surface; and a mechanised viewing system that is capable of automatically providing the camera different successive views of said surface; such that multiple pictures may be taken of said surface from multiple different viewing positions by each said camera.

Preferably, the mirror system mounting rotates about an axis collinear with the axis of the camera lens.

This type of system is smaller and more portable than the photogrammetry systems of the prior art, but nevertheless provide an accurate scan of the surface that allows e.g. an accurate sleep apnoea mask to be created from a scan of a patient's nose.

Preferably, the studio includes a portable light isolation enclosure that allows the insertion of said body surface and can be sealed for light exclusion around said body surface. Advantageously, one or more mirrors are placed inside the enclosure between the surface and the camera and oriented to allow the photographs to be taken via a periscope-like arrangement. The surface surrounding the opening for viewing the body part preferably has a flat colour so the photogrammetry matching software will ignore this region to save processing time.

According to another aspect of the invention, there is provided a method of capturing a position cloud of points on the surface of a part of a human subject, wherein said surface is prepared by coating with a texturiser; then said subject engages said surface with a portable studio as defined above; then several high-resolution digital photographs are taken of said surface; said photographs are processed by a photogrammetry software program into a point cloud by reference to particular points on said texturiser surface.

The texturiser may be a suitably textured and supple adhesive tape; or a textured paste or cream that is smeared on said surface; or an easily shaped loose mesh that is adhered to the surface; or a number of spheres attached to said surface; or one or more coloured paints. It is important that the type of texturiser selected does not deform said surface.

In an alternative embodiment, the body surface is pressed against a transparent deformable bladder inside said portable studio, or the like, and said photographs of said surface are taken through said bladder. The bladder is intended to apply a load to said surface to appropriately deform it so as to obtain the shape of the surface under similar loading. This is applicable, for example, in digitizing the sole of a foot to create an orthotic device.

Now will be described, by way of a specific, non-limiting example, a preferred embodiment of the invention with reference to the drawings.

DETAILED DESCRIPTION OF THE INVENTION

Figure 1:
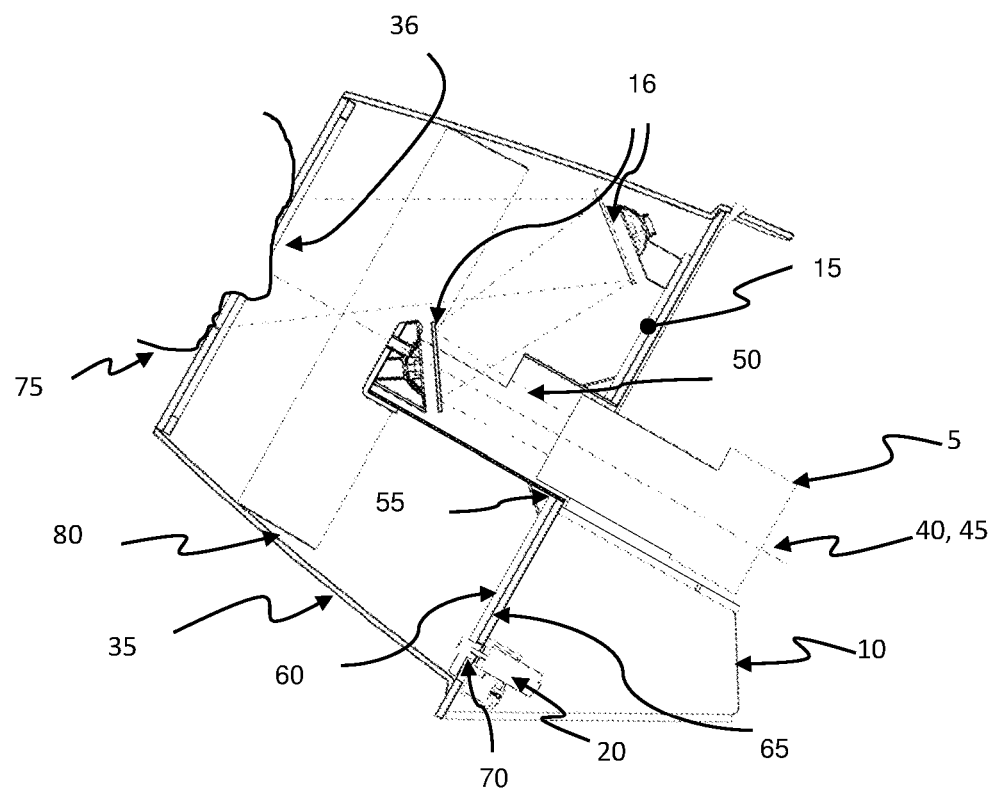
FIG. 1 is a schematic cross-section of a portable photogrammetry studio according to the invention.
Figure 2:
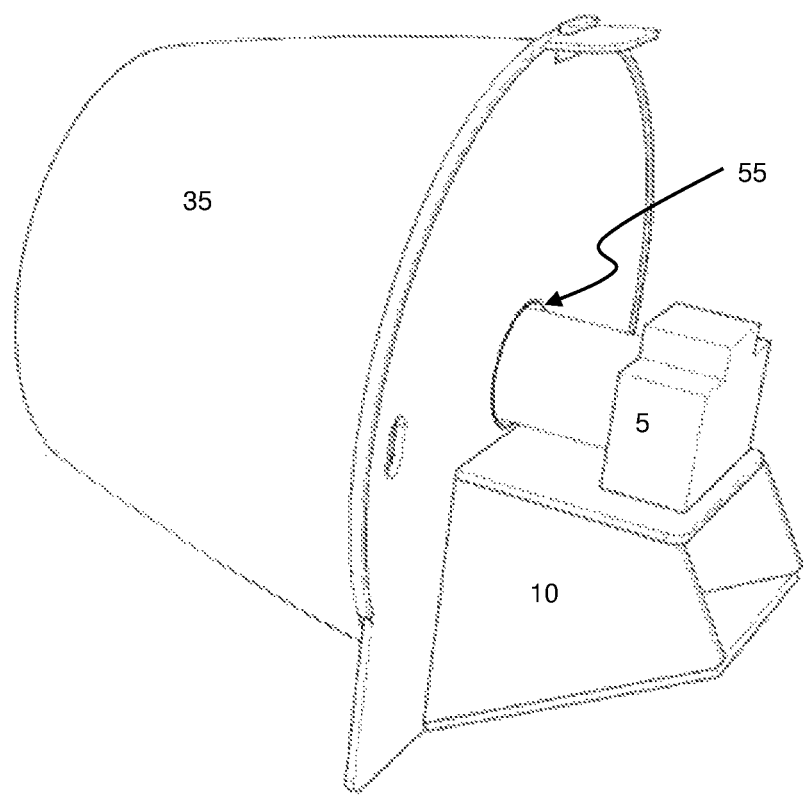
FIG. 2 is an external view of a portable photogrammetry studio according to the invention.
Figure 3:
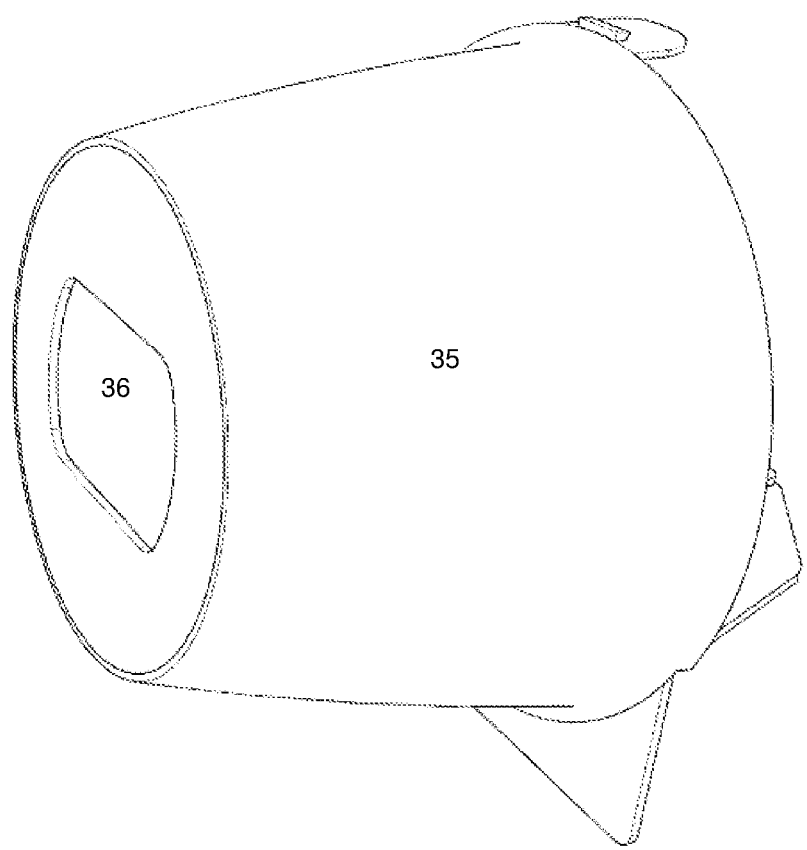
FIG. 3 is an external view of a portable photogrammetry studio according to the invention.
Figure 4:
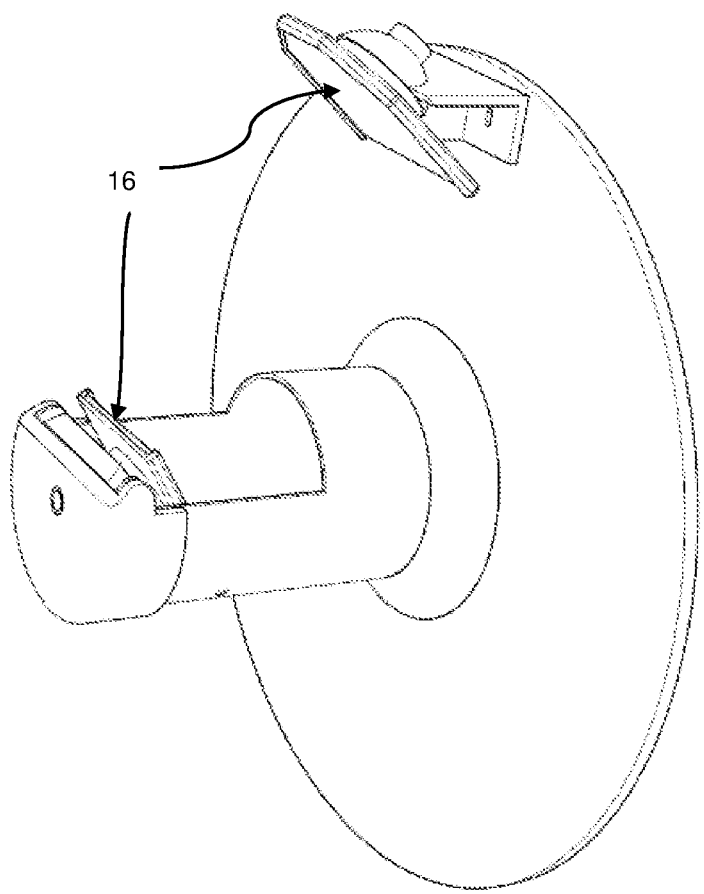
FIG. 4 is a partially exploded view of a portable photogrammetry studio according to the invention.
Figure 5:
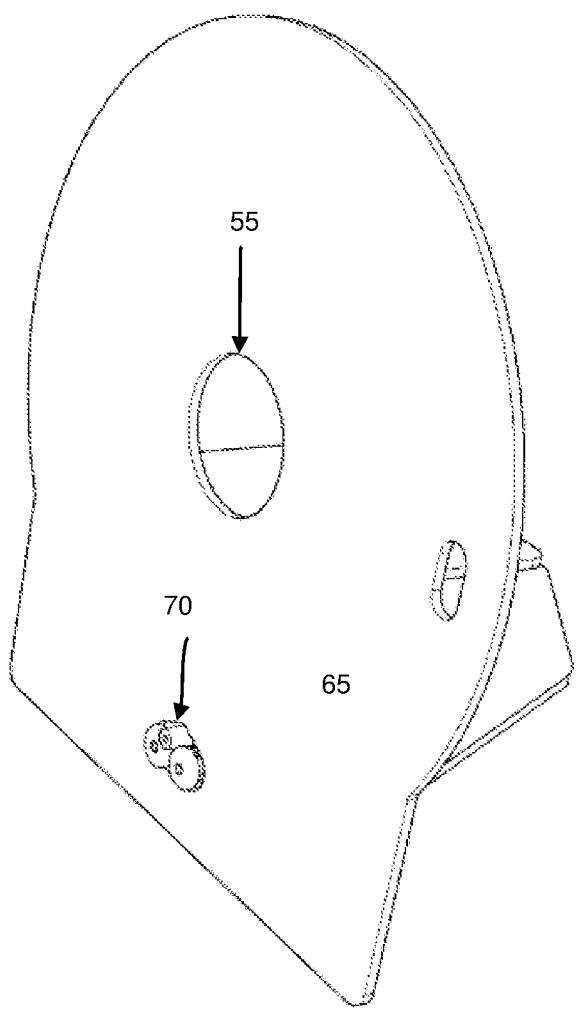
FIG. 5 is a partially exploded view of a portable photogrammetry studio according to the invention.
Figure 6:
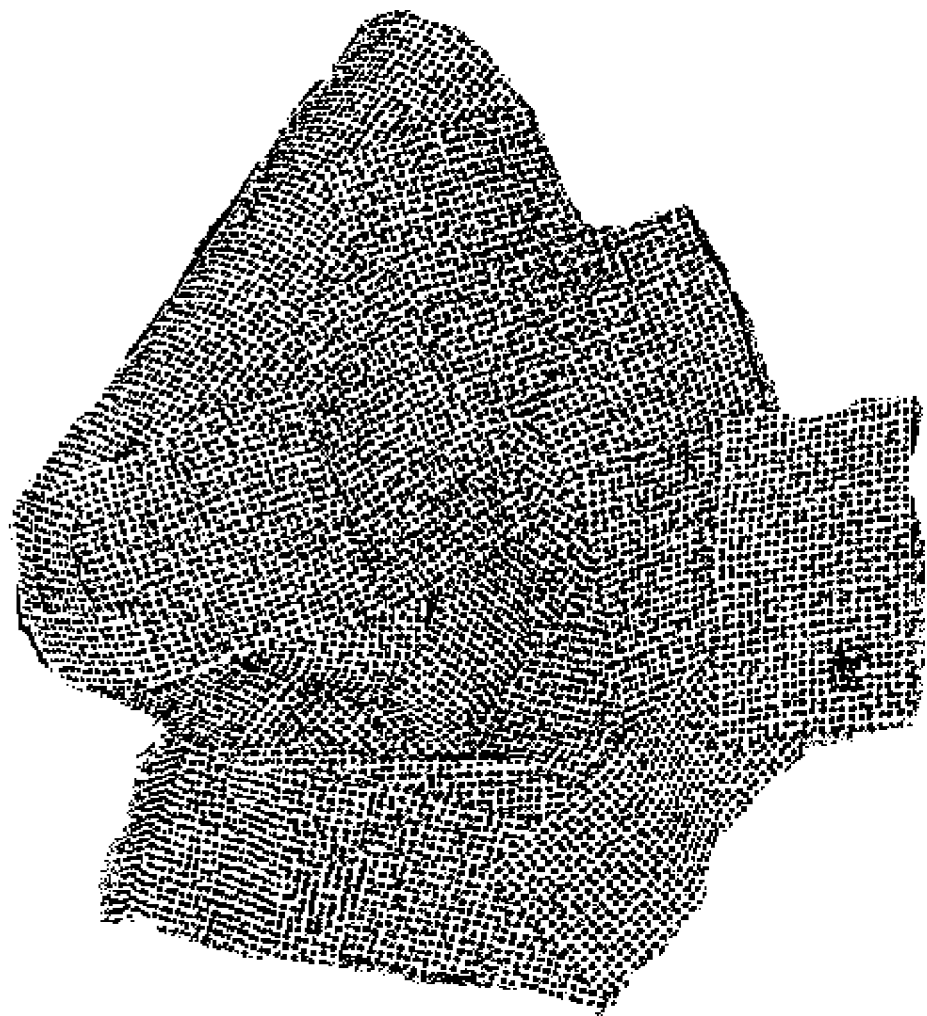
FIG. 6 is an enhanced photograph of a texturized human nose taken by the photogrammetry studio according to the invention.

A preferred embodiment of a portable photogrammetry studio according to the invention, as shown in FIGS. 1 to 5, includes a high resolution digital camera 5, a support structure 10, a rotatable mirror platform 15 supporting two mirrors 16, a motor drive mechanism 20, a control system (not shown), a power supply (not shown) and a light isolation enclosure 35 with an opening 36 through which e.g. a human nose may be inserted. The light source is provided by a cylindrical LED array 80.

The digital camera 5 is mounted so as to align its lens axis 40 with the rotation axis 45 of the mirror platform 15. The mirrors 16 are aligned relatively to reflect the position of the opening 36 into the focal axis of the camera 5, so that whatever is inserted into the opening 36 will be in the direct view of the camera lens.

The mirror platform 15 has a tube-like element 50 that extends into a corresponding hole 55 in the support structure 10. The circular disk portion 60 rests flat on the main face 65 of the support structure 10 and sits on a drive wheel 70 of the motor drive mechanism 20. This design provides fairly accurate rotational movement for the two mirrors.

The motor drive mechanism 20 is able to rotate the mirror platform 15 to present different views of the surface being photographed 75 to the camera 5.

The subject surface and the mounted assembly are positioned and oriented such that the rotation of the mirror system will present the subject surface to the camera. A subject presents the body surface to be scanned at an open end of the enclosure, and a sequence of images are taken as the mirror system rotates through 360°.

The sequence of images are processed by photogrammetry software which first matches points between neighbouring images, then calibrates the relative camera positions, orientations and lens settings and finally triangulates the corresponding 3D surface points. The algorithms are designed to minimize any mathematical error terms at each step. The software effectively calibrates the camera's position, with the benefit that the subject surface can move a little between photographs although the shape of the surface needs to be maintained. Photogrammetry software is well documented in the literature: in this case the software is known commercially as 'insight3d', as supplied by sourceforge.net.

Hardware cost may be minimized by using a rotating periscope with a single camera rather than using multiple cameras.

The camera lens is chosen to provide a suitable subject-to-lens distance for a compact design. A macro lens is a suitable lens for common consumer digital cameras.

An optional sensor system, not shown, may provide the control system with adequate information about the mirror platform's position to allow the control system to control the motor so as to move the mirror platform successively to the required position for each photograph.

Alternatively, the control system may use manual input to control the motor; or the motor may be driven for specific periods to achieve the required positions.

The mirror mounts have a spherical partial ball-joint design to allow for accurate alignment of each mirror. The centre of the spherical contact surface is designed to be at or near the centre of the reflective mirror surface. A bolt is used to hold the ball-joint together. It can be loosened to permit reorientation of the mirror then the bolt tightened to lock the mirror in place.

The surfaces of the support structure and the mirror platform are preferably covered with a white non-glossy sheet or paint to aid in providing bright and diffuse lighting to the surface being photographed.

The light isolation enclosure is designed to easily fit onto and rest on the support structure. White LED strip lights of about 30 W output are mounted inside the enclosure with a small electrical cable and plug that can be plugged in to a socket mounted in the support structure. A transparent protective polycarbonate plastic cover is attached over the LED strip lights to protect them during transport. The internal surface of the enclosure is preferably covered with a reflective tape to aid in providing bright and diffuse light.

An opening is provided in the light enclosure for viewing of the surface to be photographed. When photographing a nasal region, the person to be photographed rests their forehead and chin on the outer flat surface of enclosure. The opening may allow a small amount of external light in to the inner chamber but the lighting on the face is dominated by the internal light so changes in external light due to shadows, etc. have negligible effect.

The portable photogrammetry studio and texturiser provides a simple, easy to use and cost effective way to take multiple views of a surface, filling the photographed views with the image of the surface and having a colour texture with consistent lighting, exposure and focus and an adequate depth-of-field to provide a set of photographs best suited to processing by photogrammetry software. Further, automatic processing of the photographs by the portable photogrammetry studio significantly reduces the amount of data so the results are more easily sent over the internet for use elsewhere.

In an alternative embodiment, the outer rotating mirror may be replaced with multiple mirrors affixed to the support structure, each mirror providing one view. The central mirror then rotates to successively align the view from each outer mirror with the camera lens.

A further alternative embodiment has outer mirrors arranged to provide views that are not just in a conical arrangement about the centre of the photographed surface, as described above, but provide other angles as well. The central mirror then rotates about two axes instead of just one to successively align the view from each outer mirror with the camera lens.

In another embodiment a camera with a suitable macro lens for close up shots may be moved by an automated mechanism to successive positions to take the required set of photographs. No mirrors would be required in this device.

A texture may be applied to the body part surface prior to presenting it at the enclosure opening. The operator then commences the photogrammetry sequence and processes the images to produce a point cloud. The point cloud may then be transmitted, e.g. by email, by the control system to a fabrication facility to produce the body-engaging part.

The resolution and accuracy of the resulting point cloud is affected by a number of factors related to the quality of the photographs. Ideally the photographs would have the subject surface fully in focus with consistent lighting between photographs and minimal or no visible highlights. A matt surface helps to minimize highlights. The subject surface preferably is texturized to enhance the varying colour and/or brightness used by the point matching algorithms.

A higher resolution camera, i.e. one having a resolution of 18 megapixels provides improved results but at a higher equipment cost. Consumer cameras generally have a single image sensor with a Bayer red-green-blue pattern filter to provide colour images at lower cost. Software processes and converts the raw Bayer image into relevant formats used by computers and printers. Photogrammetry software generally uses the more common formats although algorithms targeted to use Bayer images could provide improved results.

The point cloud generated by the photogrammetry needs to be scaled to the correct size. Also, since the photographs are taken from a rotating sequence of views the photogrammetry algorithm may produce a mirror image of the surface. To assist in sizing and possibly mirroring the point cloud to its correct size and direction one or more phantom devices or phantom points are used. A phantom is a known physical item or defining marks that are included in the photographs for sizing and mirroring purposes. The phantom can be identified from the point cloud and, given there is at least one known dimension, the point cloud generated by the photogrammetry can be scaled accordingly. Likewise a phantom with a left/right handedness can be used to ensure the point cloud is mirrored, if necessary.

A lens having an optical performance that can focus to a resolution that matches, or exceeds, the image sensor's pixel size is required to produce quality images. Monochromatic lenses are less expensive than lenses providing correction for chromatic aberration and should still provide adequate results.

In one embodiment of the invention each optical component is designed to work best at a given monochromatic frequency, as monochromatic light sources, lenses and image sensors are typically less expensive and/or more efficient than coloured versions.

The taking of a fixed zoom photograph, as in the present invention, involves four fundamental camera settings; the film speed, the aperture, the shutter speed and the focussing distance. The focussing distance is best set to a plane around the middle of the depth of the subject surface. A high speed photograph minimizes the potential for motion blur due to movement or vibration of the body part, the periscope and/or the camera. The amount of light exposure is dependent on the brightness of the subject, the shutter speed and the aperture setting. Faster shutter speeds require larger apertures, but larger apertures decrease the depth of field which will, at some point, cause blurring of the image further from the plane of focus. In an optimized system an image sensor can be used to determine the film speed, and the position of the body part determines the required depth of field which in turn determines the aperture setting.

Adequate lighting is then used to allow for a suitable shutter speed. Smaller apertures also allow for smaller and lower cost lenses. In practice, with common lenses, the optimal settings are exceeded by the use of bright lighting.

In an alternative embodiment, very bright lights may be used without a full enclosure. The very bright lights can assist in minimising point cloud errors resulting from any changes of external lighting and/or shadowing between successive photographs.

In another embodiment of the present invention a tilt, shift or tilt-shift lens system may be used to optimize the location of the focal plane in relation to the body part for the sequence of images. Notably, a fixed shifted lens could maintain the same focal plane for all images resulting from a rotating periscope directed at a target point.

A mini-PC or similar may be used to control the system, along with a microcontroller system, to operate the device. The device uses Wi-Fi to connect to a local network that in turn connects to the internet. In practice, setting up the device involves setting up the mini-PC's Wi-Fi connection. Everything else can be automated.

To capture a point cloud of a person's nose for the purpose of creating a personalised CPAP mask adaptor, for example, the operator may first apply a texture, such as applying a suitably textured tape to or face painting the person's face. The person then places their nose into the opening in the device and the operator starts the image capture sequence. The device operates the lights, camera and rotation motor to take the sequence of photographs then generates a suitable audible or visual signal when completed. The mini-PC processes the images to generate the point cloud then emails the point cloud to the adaptor fabrication facility, where a 3D printed replica of the person's nose surface can be created for use in e.g. a sleep apnoea mask.

In one preferred embodiment the mini-PC communicates with the microcontroller system and the camera via USB. The mini-PC can instruct the microcontroller system to turn the lights on and off and to operate the motor to drive the mirror system. Once the body part is textured and positioned correctly the operator presses a button to start the sequence. The microcontroller detects the button press and communicates this event to the mini-PC. The mini-PC then generates appropriate instructions to the microcontroller system and the camera to turn on the lights, take the first photograph, rotate the mirror system to the next position, take the next photograph, repeat until all photographs are taken, turn off the lights and generate a sound to indicate the photography process is completed. The mini-PC then processes the photographs according to the photogrammetry algorithms described previously.

Photogrammetry techniques often employ spheres attached to a surface for accurate positioning, as spheres appear as a circle or a slightly distorted circle in a photograph. Software can determine the outline of a sphere and then pinpoint the centre. In the film industry actor's movements are captured using live photogrammetry of spheres attached to a body suit that the actor wears. Instead of a texture being applied to the surface a layer of small spheres could be used along with appropriate photogrammetry software. For example, the 'hundreds-and-thousands' type candy stuck onto a person's face using e.g. honey provides an excellent layer of spheres which is not only non-toxic but edible!

A negative or positive cast or similar replica of the relevant body part could be made and the casting used to by the invention to produce a point cloud.

Alternatively, the body part may be pressed against a transparent bladder which takes the shape of the body part and can also provide an even pressure to deform the body part from its undeformed shape. The region of the bladder nearer to the body part would have a suitable texture for photogrammetry. The rotating periscope would view the textured surface through the bladder's fluid. The camera and periscope could be internal or external to the bladder.

For example, in podiatry the undeformed shape of the unloaded surface of the sole of the foot is not ideal. Preferably the foot is deformed by an even load while supporting the normal weight of the body. By standing with one foot on a bladder filled with water the foot is evenly loaded and deformed accordingly. Photos taken through the fluid of the bladder's skin that is in contact with the foot are used to produce a point cloud of the appropriately deformed shape.

It will be appreciated by those skilled in the art that the above described embodiment is merely one example of how the inventive concept can be implemented. It will be understood that other embodiments may be conceived that, while differing in their detail, nevertheless fall within the same inventive concept and represent the same invention.

The invention claimed is:

1. A portable photogrammetry studio for topographical digitisation of at least a stationary human nose, the studio comprising:
    a digital camera to photograph said stationary human nose;
    one or more light sources capable of illuminating said stationary human nose, and configured to provide consistent colour and brightness between photographs of said stationary human nose;
    a mechanised viewing system that is capable of providing different views of said stationary human nose to said camera, such that multiple photographs may be taken of said stationary human nose from multiple different positions by said camera; and
    a portable light isolation enclosure that allows the insertion of said human nose through an opening in the enclosure and at least partially reduces external light entering the enclosure such that lighting on said stationary human nose is dominated by the light emitted from the one or more light sources, so that changes in the external light have negligible effect on the photographs taken of said stationary human nose,
    wherein said mechanised viewing system includes a rotatable mirror system that is capable of providing different views of said stationary human nose to said camera while said stationary human nose is positioned through said opening, and
    wherein internal surfaces that oppose said opening of said enclosure comprise non-glossy surfaces and said one or more light sources is positioned within said enclosure around said opening so as to illuminate said stationary human nose with diffuse lighting from all directions due to diffuse reflections from said non-glossy surfaces, the diffuse lighting being a lighting that produces photographs with minimal or no visible highlights.

2. The portable studio of claim 1, wherein the rotatable mirror system rotates about an axis collinear with the axis of the camera lens.

3. The portable studio of claim 1, wherein mirrors of the rotatable mirror system are positioned to allow the photographs to be taken via a rotating periscope.

4. The portable studio of claim 1, wherein an internal surface of the enclosure is covered with a reflective tape.

5. The portable studio of claim 1, wherein the one or more light sources are a cylindrical LED array or white LED strip lights of about 30 W output.

6. The portable studio of claim 1, wherein the rotatable mirror system supports two mirrors.

7. The portable studio of claim 1, wherein the rotatable mirror system is rotated by a motor drive mechanism.

8. A sequence of photographs taken by the portable photogrammetry studio of claim 1 for processing by photogrammetry software by:
    matching points between neighbouring images;
    calibrating relative camera positions, orientations and lens settings; and
    triangulating corresponding 3D surface points to generate a point cloud.

9. The portable studio of claim 1, wherein said non-glossy surfaces that oppose said opening of said enclosure at least include a rotatable mirror platform of the rotatable mirror system.

10. The portable studio of claim 9, wherein the rotatable mirror platform is covered with a white non-glossy sheet or paint.

11. A method of capturing a position cloud of points on a stationary human nose of a patient, the method comprising:
    preparing said stationary human nose by coating with an opaque texturizer to produce a texturised surface on said stationary human nose that does not deform said stationary human nose;
    then said patient engages said stationary human nose with an opening of a portable photogrammetry studio, said portable photogrammetry studio comprising:
        a digital camera to photograph said texturised surface of said stationary human nose;
        one or more light sources capable of illuminating said stationary human nose, and configured to provide consistent colour and brightness between photographs of said stationary human nose;
        a mechanised viewing system that is capable of providing different views of said stationary human nose to said camera such that multiple photographs may be taken of said stationary human nose from multiple different positions by said camera; and
        a portable light isolation enclosure that contains the opening to allow the insertion of said stationary human nose through the opening, the enclosure at least partially reducing external light entering the enclosure such that lighting on said stationary human nose is dominated by the light emitted from the one or more light sources, so that changes in the external light have negligible effect on the photographs taken of said stationary human nose, wherein said mechanised viewing system includes a rotatable mirror system that is capable of providing different views of said stationary human nose to said camera while said stationary human nose is positioned through said opening, and wherein internal surfaces that oppose said opening of said enclosure comprise non-glossy surfaces and said one or more light sources is positioned within said enclosure around said opening so as to illuminate said stationary human nose with diffuse lighting from all directions due to diffuse reflections from said non-glossy surfaces, the diffuse lighting being a lighting that produces photographs with minimal or no visible highlights;

then several digital photographs are taken of said stationary human nose using said camera and said mechanised viewing system while said one or more light sources illuminate said stationary human nose; and said photographs are processed by a photogrammetry software program into a point cloud by reference to particular points on said texturised surface.

12. The method of claim 11, wherein the opaque texturiser is an adhesive tape.

13. The method of claim 11, wherein the opaque texturiser is a number of spheres attached to said texturised surface.

14. The method of claim 11 wherein the opaque texturiser is a paint.

15. The method of claim 11, wherein said non-glossy surfaces that oppose said opening of said enclosure at least include a rotatable mirror platform of the rotatable mirror system.

16. The method of claim 15, wherein the rotatable mirror platform is covered with a white non-glossy sheet or paint.

17. A portable photogrammetry studio for topographical digitisation of at least a stationary human nose, the studio comprising:
 a digital camera to photograph said stationary human nose;
 a portable light isolation enclosure that allows the insertion of said stationary human nose through an opening in said enclosure;
 one or more light sources positioned within said enclosure around said opening and capable of illuminating said stationary human nose; and
 a mechanised viewing system comprising a rotatable mirror system within said enclosure that is capable of providing different views of said stationary human nose to said camera such that multiple photographs may be taken of said stationary human nose from multiple different positions by said camera,
 wherein said portable light isolation enclosure at least partially reduces external light entering the enclosure such that lighting on said stationary human nose is dominated by light emitted from said one or more light sources, so that changes in the external light have negligible effect on the photographs taken of said stationary human nose; and
 wherein internal surfaces that oppose said opening of said enclosure comprise non-glossy surfaces to aid in providing diffuse lighting to said stationary human nose due to diffuse reflections from said non-glossy surfaces, the diffuse lighting being a lighting that produces consistent colour and brightness between said multiple photographs taken from multiple different positions with minimal or no visible highlights.

18. The portable studio of claim 17, wherein said non-glossy surfaces that oppose said opening of said enclosure at least include a rotatable mirror platform of the rotatable mirror system.

19. The portable studio of claim 18, wherein the rotatable mirror platform is covered with a white non-glossy sheet or paint.

* * * * *